(12) United States Patent
Liddell

(10) Patent No.: US 8,889,852 B2
(45) Date of Patent: Nov. 18, 2014

(54) PLASMID DNA EXTRACTION PROCESS

(75) Inventor: John Macdonald Liddell, Billingham (GB)

(73) Assignee: Fujifilm Diosynth Biotechnologies UK Limited, Billingham (GB)

(\*) Notice: Subject to any disclaimer, the term of this patent is extended or adjusted under 35 U.S.C. 154(b) by 124 days.

(21) Appl. No.: 13/380,699

(22) PCT Filed: Jul. 22, 2010

(86) PCT No.: PCT/GB2010/001388
§ 371 (c)(1),
(2), (4) Date: Jan. 19, 2012

(87) PCT Pub. No.: WO2011/012841
PCT Pub. Date: Feb. 3, 2011

(65) Prior Publication Data
US 2012/0123110 A1    May 17, 2012

(30) Foreign Application Priority Data
Jul. 29, 2009  (GB) .................................. 0913160.8

(51) Int. Cl.
*C07H 21/00*  (2006.01)
*C12N 15/10*  (2006.01)

(52) U.S. Cl.
CPC ................................ *C12N 15/1003* (2013.01)
USPC .................. 536/25.41; 536/25.4; 536/25.42

(58) Field of Classification Search
None
See application file for complete search history.

(56) References Cited

U.S. PATENT DOCUMENTS 6,197,553 B1 \* 3/2001 Lee et al. ..................... 435/91.1
2002/0001829 A1   1/2002 Lee et al.

OTHER PUBLICATIONS

Holmes, A Rapid Boiling Method for the Preparation of Bacterial Plasmids, Analytical Biochemistry, 114, 193-197, 1981.
Zhu, A Continuous Method for the Large-Scale Extraction of Plasmid DNA by Modified Boiling Lysis, Nature Protocols, 1, 3088-3093, 2006.
Rees, Effects of Heat Shock on Gram Negative Bacteria: Use of Lysis by Sodium Dodecyl Sulphate as a Probe for the Integrity of DNA, Bioseparation, 6, 125-132, 1996.

\* cited by examiner

*Primary Examiner* — Patrick Lewis
(74) *Attorney, Agent, or Firm* — Morgan, Lewis & Bockius LLP

(57) ABSTRACT

A process for the extraction of pDNA from cells is provided. In one aspect, the process comprises heating a liquid comprising the cells to an average temperature of from 95° C. to about 120° C. for a time of less than 10 seconds. In certain preferred aspects, the pDNA is extracted by the use of flow-through apparatus.

18 Claims, 4 Drawing Sheets

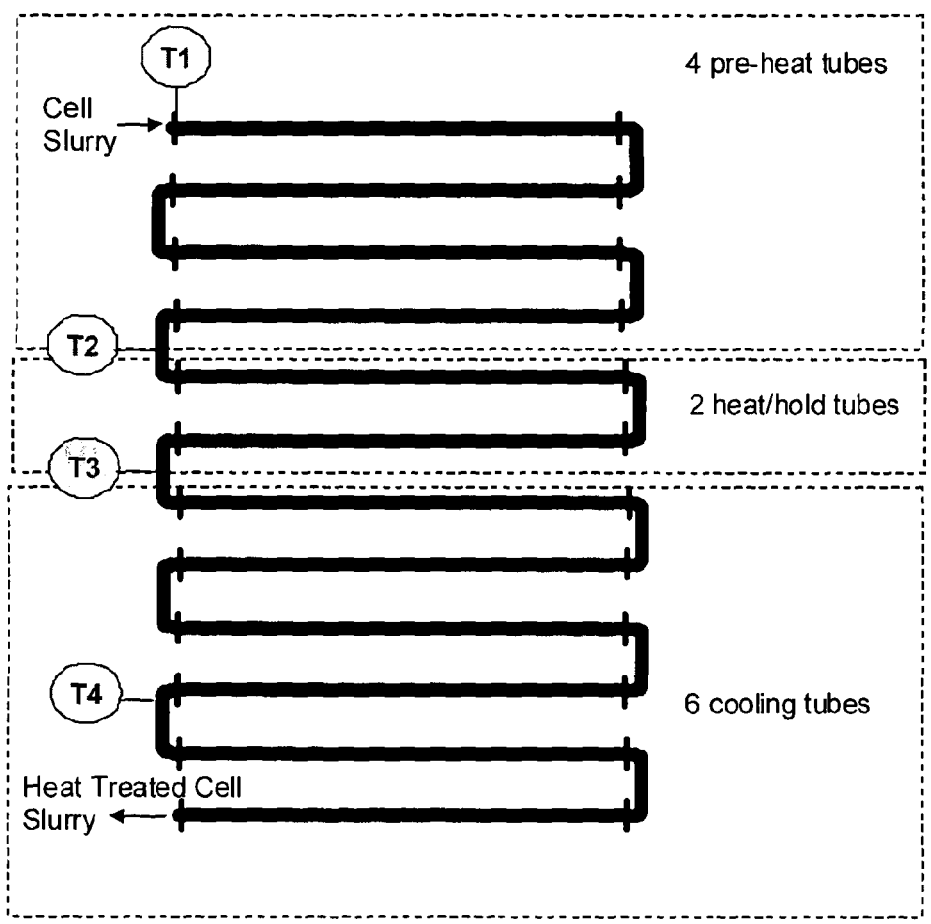
Figure 1: Schematic of Heat Treatment Apparatus Configured as Described in Comparative Example Figure 2: Agarose gel electrophoresis analysis

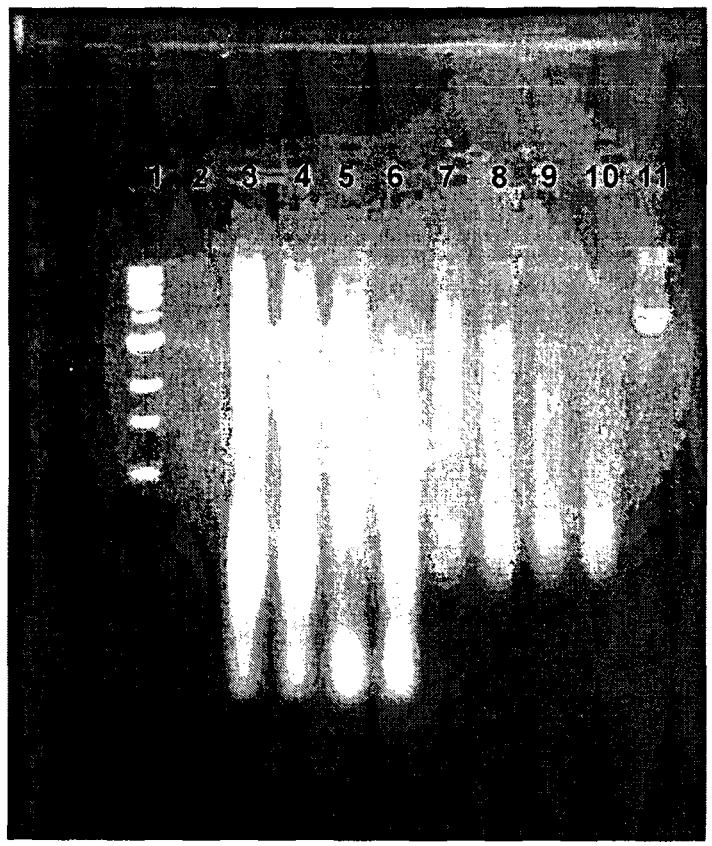

Lane 1: Molecular Weight Markers
Lane 2: Blank
Lane 3: Heat treatment Condition C – ~8 seconds Hold, Hold $T_{average}$ = 122°C
Lane 4: Heat treatment Condition B – ~11 seconds Hold, Hold $T_{average}$ = 123.5°C
Lane 5: Heat treatment Condition A – ~16 seconds Hold, Hold $T_{average}$ = 122°C
Lane 6: Heat treatment Condition D – ~23 seconds Hold, Hold $T_{average}$ = 122°C
Lanes 7-10: 1/5 diluted Condition C replicates
Lane 11: pDNA extracted from fermentation harvest Figure 3: Schematic of Heat Treatment Apparatus Configured as Described in Example 1
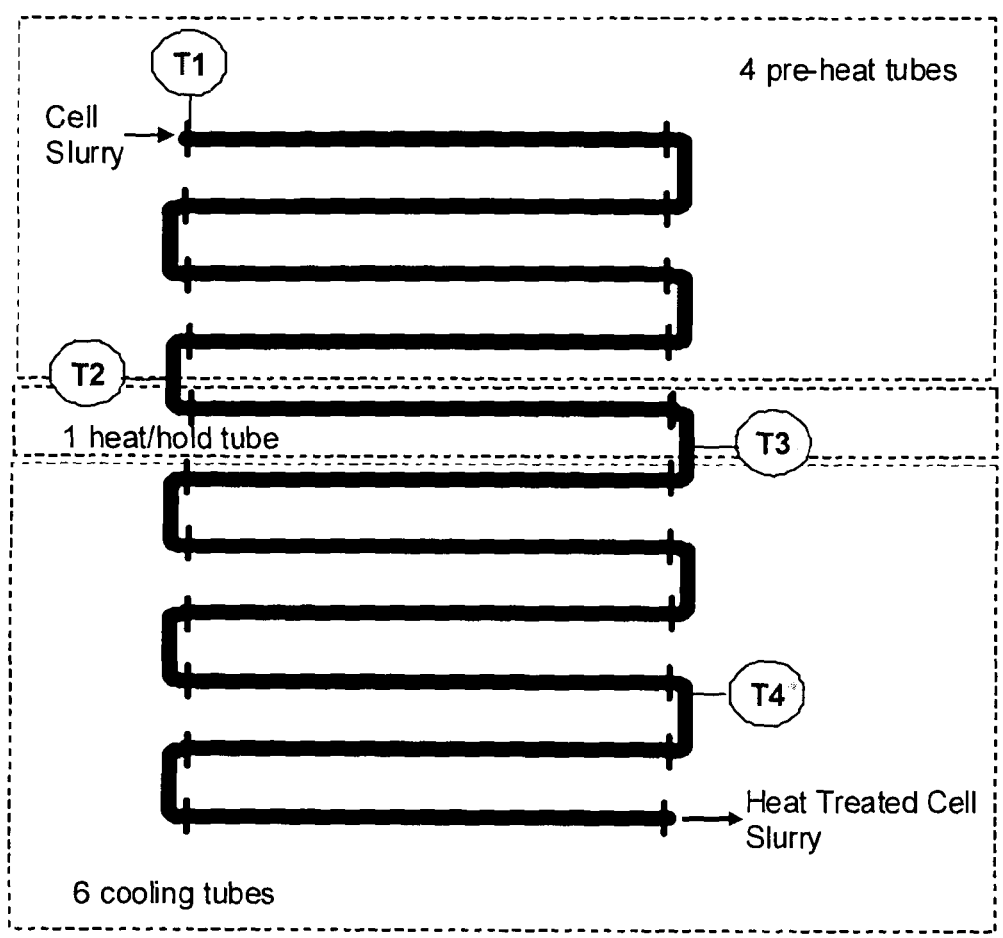

Figure 4: Agarose gel electrophoresis analysis

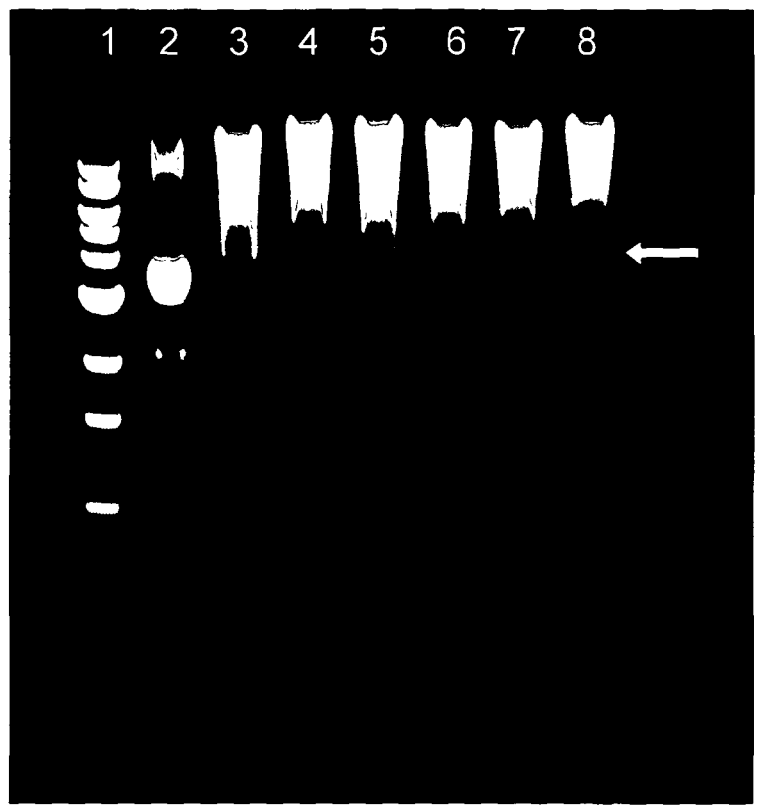

Lane 1: Molecular Weight Markers
Lane 2: pDNA extracted from fermentation harvest
Lane 3: Heat treatment Condition E – ~6 seconds Hold, Hold $T_{average}$ = 109°C
Lane 4: Heat treatment Condition F – ~4 seconds Hold, Hold $T_{average}$ = 103°C
Lane 5: Heat treatment Condition G – ~5 seconds Hold, Hold $T_{average}$ = 108.5°C
Lane 6: Heat treatment Condition H – ~6 seconds Hold, Hold $T_{average}$ = 103.5°C
Lane 7: Heat treatment Condition I – ~6 seconds Hold, Hold $T_{average}$ = 100.5°C
Lane 8: Heat treatment Condition J – ~4 seconds Hold, Hold $T_{average}$ = 96.5°C

PLASMID DNA EXTRACTION PROCESS

RELATED APPLICATIONS

The present application is a U.S. National Phase Application of International Application No. PCT/GB2010/001388 (filed Jul. 22, 2010) which claims priority to Great Britain Application No. 0913160.8 (Filed Jul. 29, 2009) which are hereby incorporated by reference in their entirety.

The present invention concerns a process for the extraction of plasmid DNA (pDNA) from a cell.

Many techniques for isolating pDNA from microbial fermentations are only suitable for small or laboratory scale plasmid preparations. One commonly employed procedure comprises isopycnic centrifugation using CsCl in the presence of ethidium bromide. The procedure employs expensive and harmful reagents which are unsuited to the manufacture of pDNA for therapeutic purposes. Further ethidium bromide can damage the pDNA. The method suffers from many other disadvantages rendering it unsuitable for large scale pDNA manufacture.

Holmes and Quigley (1981, Analytical Biochem., 114, pp 193-197) disclose a process for isolating and purifying plasmid DNA from bacteria which comprises boiling at about 100° C. for 20-40 seconds. In a related disclosure, U.S. Pat. No. 4,830,969, temperatures of from 60 to 105° C. for contact times of from 10 seconds to about 3 minutes are disclosed. This technique is not suitable for large scale pDNA manufacture.

US2002/0001829 discloses a method for the isolation of pDNA which comprises suspending microbial cells in modified STET buffer and heating the suspension to 70-100° C. in a flow-through heat exchanger, with temperatures of from 70 to 77° C. preferred. The level of supercoiled pDNA, the preferred form of pDNA for many applications, is taught to be diminished at temperatures above 93° C.

According to certain embodiments of the present invention, there is provided a process for the extraction of pDNA from a cell, which comprises heating a liquid comprising the cell to an average temperature of from 95° C. to about 120° C. for a time of less than 10 seconds.

According to further embodiments of the present invention, there is provided a process for the extraction of pDNA from a cell, which comprises heating a liquid comprising the cell in a flow-through apparatus to a temperature of 95° C. or more, provided that the liquid is not heated to an average temperature of greater than 120° C. for longer than 5 seconds.

pDNA which can be extracted by the process of the present invention can be produced in one or more of multiple forms, such as supercoiled, linear and open-circular (i.e. nicked or relaxed) isoforms. The supercoiled pDNA isoform has a covalently closed circular form and the pDNA is negatively supercoiled in the host cell by the action of host enzyme systems. In the open-circular isoform, one strand of the pDNA duplex is broken at one or more places. For many plasmid applications, the supercoiled isoform is most preferred and is advantageously separated from the linear and open-circular isoforms. Plasmids for gene transfer, e.g. in-vitro DNA transformation or in-vivo gene therapy, may require a high percentage of the supercoiled plasmid isoform and a low percentage of open circular isoform. Therefore, the commercial need to obtain highly purified supercoiled plasmid DNA is extremely high. Methods to convert the open circular plasmid isoform to the supercoiled isoform are known in the art. For example, US20060057683 discloses a process where this is achieved enzymatically. Thus, in certain embodiments, following extraction using the present invention, pDNA in the open circular isoform is converted using methods established in the art to the supercoiled isoform.

pDNA extracted by the process of the present invention is commonly produced by the growth and harvesting of host cells, and preferably by microbial fermentation of recombinant microorganisms. The most preferred host cell is *E. coli* although many other types of cells are known to carry plasmids. This includes other bacteria, yeast and higher eukaryotic cells. Examples include the yeasts *Saccharomyces cerevisiae* and *Kluyveromyces lactis*, filamentous fungi such as *Neurospora* spp and the algae *Chamydomomas*.

Methods for the production of pDNA are well known in the art. pDNA may be natural or artificial, for example, cloning vectors carrying foreign DNA inserts. In many embodiments, the pDNA is in the size range of 1 kilobase to 50 kilobases. For example pDNA encoding expressed interfering RNA is typically in the size range of 3 kilobases to 4 kilobases.

Liquids comprising cells which can be employed in the process of the present invention include culture broths in which the cells have been grown. In many embodiments, the liquid is a suspension of the cells prepared by harvesting the cells from the culture broth, and then resuspension of the cells, preferably in an aqueous buffer solution. Cells are harvested from the liquid by methods well known in the art, such as centrifugation or microfiltration.

When resuspension of cells is employed, the cells are preferably resuspended in an aqueous buffer, commonly with a pH in the range of from 4 to 10, and preferably at around neutral pH, for example from 7 to 9. The buffer salt concentration is commonly in the range of from 10-100 mM, such as in the range 20-80 mM. In certain embodiments, a particularly suitable buffer is 50 mM Tris HCl at pH 8. The buffer may contain chelating agents such as EDTA to maintain metal ions in solution and solubilise cell wall cations such as calcium. The resuspension buffer may also contain other compounds to assist in pDNA release such as polyols, for example sucrose, commonly in the range of from 2 to 15% w/w, preferably from 5 to 10% w/w; surfactants, for example Triton™ X-100 commonly in the range of from 1 to 5% w/w, preferably from 1 to 3% w/w; and/or chaotropes, for example urea, commonly at a concentration in the range of from 0.5 to 8M, preferably from 1 to 3M.

When the liquid comprising cells is a culture broth, the pH may be adjusted to a pH in the range of from 4 to 10, and preferably at around neutral pH, for example from 7 to 9. Chelating agents and other compounds to assist pDNA release, as described above for cell resuspension, may be employed if desired.

The process of the present invention does not require the use of cell wall lytic enzymes, such as lysozyme to achieve pDNA extraction, but such enzymes may be employed if desired.

The process of the present invention is suited to the processing of pDNA produced at small, medium or large scale. Small scale is typically regarded as a scale of up to 2 liters, commonly employing shake flasks. Medium scale is typically regarded as a scale of from 2 liters to 500 liters. Large scale is typically regarded as a scale of greater than 500 liters, such as up to 100,000 liters, for example from 1000 liters to 10,000 liters.

In the process of the present invention, the liquid comprising cells is heated to 95° C. or more, with temperatures greater than 95° C. being preferred, from its initial temperature, most commonly a temperature at which the liquid is stable for significant periods of time, such as for about an hour up to at least several days depending upon the precise nature of the production process being operated. In some embodiments, for example where the liquid comprises a culture broth in which the cells have been grown, the initial temperature is in the range of from 30 to 45° C., such as about 35-38° C. In other embodiments, the initial temperature is in the range of from about 2 to about 10° C., for example where the liquid has been chilled, either in the form of the culture broth, or as a resuspension of the cells. In many embodiments, the initial temperature is in the range of from 2 to 30° C., and is often ambient temperature, for example from 15 to 25° C. The heating is most preferably effected rapidly, for example over a period of less than 10, especially less than 5 seconds. After maintaining the liquid at a temperature in the desired range for the desired length of time, the liquid is cooled, commonly to a temperature at which the liquid is stable, and preferably a temperature in the range of from 10 to 45° C. Cooling is preferably effected rapidly, for example over a period of up to 40 seconds. In certain embodiments, the liquid is cooled to a temperature below 70° C. in 20 seconds or less, such as from 10 to 15 seconds.

In many embodiments, the liquid is maintained at a temperature above 95° C. and up to 110° C., preferably from 96° C. to 110° C., especially from 100° C. to 109° C., for from 2 to 6 seconds. In other embodiments, the liquid is maintained at a temperature of from 115° C. to 120° C. for from 1 to 3 seconds. In yet further embodiments, the liquid is maintained at a temperature of from 120° C. to 130° C. for from 0.5 to 1.5 seconds.

It is particularly preferred that the process of the present invention is carried out using flow-through apparatus. Such apparatus commonly comprises a heating zone, where the liquid is heated from the initial temperature to a temperature of greater than 95° C., a holding zone, where the liquid is held at the desired temperature for the desired time, and a cooling zone, where the liquid is cooled to the desired temperature. Most preferably the liquid flows through a tube passing through the heating, holding and cooling zones, with the temperatures applied to the tube and the liquid flow rate adjusted to provide the desired conditions. In certain preferred embodiments, the tube incorporates mixing elements, such as static mixing elements, in order to improve the uniformity of heating and cooling of the liquid.

Flow-through apparatus, especially heat exchange apparatus, suitable for carrying out the process of the present invention is well known in the art. Examples include High Temperature Short Time heat exchangers commonly employed in the UHT pasteurisation industry, and Continuous Media Sterilisation apparatus. Commercially available apparatus includes the Armfield FT74X UHT/HTST System and the Armfield FT94X UHT/HTST Mini-pilot System (Armfield Ltd, Ringwood, UK). Larger scale apparatus is available from, for example, Schmidt SigmaTherm Systems (API Heat Transfer, Buffalo, N.Y., USA), IPEC (Wisconsin, USA) and GEA Process Engineering Inc (Colombia, Md., USA). It will be evident to those skilled in the art that suitable apparatus for use in the present invention may easily be modified or individually designed and constructed to match particular processing requirements, e.g. fermentation volume and centrifugation capacity available to process fermentation broth available.

pDNA which has been extracted by the process of the present invention is commonly purified and isolated by methods known in the art. Examples of such methods include centrifugation, filtration, chromatography, diafiltration, precipitation such as addition of CTAB or as described in Lander et al U.S. Pat. No. 6,797,476 and two phase aqueous extraction as described by Hubbuch et al, Biotechnol Appl Biochem. (2005) 42 pp 57-66.

Large cell debris, protein and most genomic DNA is commonly removed by centrifugation. An optional treatment with RNase may be employed, and the pDNA may be filtered to further remove small debris, for example filtration through a 0.45 micron filter.

Further impurities may be removed by diafiltration, commonly using an ultrafiltration membrane having a molecular weight cut off selected according to the size of the pDNA.

Chromatographic methods which can be employed include charged membrane chromatography (for example as described in Endres et al, Biotechnol Appl Biochem. (2003) 37 pp 259-66), monolith chromatography (for example as described in Stancar et al, Adv Biochem Eng Biotechnol. (2002) 76: pp 49-85), anion exchange chromatography and reversed phase chromatography. In many embodiments, both anion exchange and reversed phase methods are employed. It is preferred that at least one, and preferably each of centrifugation, filtration and diafiltration steps are employed prior to chromatography. Examples of suitable anion exchange matrices include those available from POROS Anion Exchange Resins, Qiagen, Toso Haas, Sterogene, Spherodex, Nucleopac, and GE Healthcare. Examples of suitable reversed phase matrices include those available from POROS, Polymer Labs, Toso Haas, GE Healthcare, PQ Corp., Zorbax, BioSepra resins, BioSepra Hyper D resins, BioSepra Q-Hyper D resins and Amicon. Preferably, anion exchange chromatography precedes reversed phase chromatography.

BRIEF DESCRIPTION OF THE FIGURES

FIG. 1 provides a schematic of the layout of the heat treatment apparatus according to an embodiment of the present invention.

FIG. 2 shows the results of an agarose gel electrophoresis analysis.

FIG. 3 provides a schematic of the layout of the heat treatment apparatus according to an embodiment of the present invention.

FIG. 4 shows the results of an agarose gel electrophoresis analysis.

Purified pDNA may be concentrated and/or diafiltered to reduce the volume or to change the buffer, for instance to transfer the pDNA into a pharmaceutically acceptable carrier or buffer solution, optionally followed by sterilisation. Examples of pharmaceutically acceptable carriers or buffer solutions are known in the art. Methods suitable for concentrating pDNA are well known in the art and include diafiltration, alcohol precipitation and lyophilisation, with diafiltration being preferred. Methods of sterilisation which do not affect the utility of the pDNA are well known in the art, such as sterilisation by passage through a membrane having a small pore size, for example 0.2 microns and smaller.

The present invention is illustrated without limitation by the following examples.

Strain Preparation

The gene sequence for IgG-Fc protein was cloned into pCMV-Script (Stratagene Catalogue 212220). Recombinant clones containing a 5.7 Kb recombinant plasmid were identified by restriction digest and confirmed by sequencing. One plasmid clone was transformed, using electroporation into *E. coli* host strain XL-1 Blue MR (Stratagene, Catalogue 200229) to generate the recombinant *E. coli* strain. The recombinant strain, designated CLD 327, was purified and maintained in glycerol stocks at −80° C.

COMPARATIVE EXAMPLE

Batch fermentation (15 L) using CLD 327 was carried out at 30° C. and pH 7.0 using a minimal salts fermentation basal medium supplemented with glycerol and yeast extract. The dissolved oxygen set-point was 30% of saturation and was controlled by automatic adjustment of the fermenter agitation speed. Samples were taken throughout the fermentation for measurement of cell growth ($OD_{600}$). The fermentation was continued until the $OD_{600}$ reached ~30 units (prior to glycerol depletion). A sample of the fermenter culture was taken, centrifuged to separate the cell pellet from the supernatant and the cell pellet stored frozen at −20° C. The fermenter vessel contents were then cooled to ~10° C. and transferred to 1 L sealable centrifuge bottles and the cells collected by batch centrifugation at 8-12° C. The recovered cell pellets were re-suspended to a volume of 12 L using cold (2-8° C.) buffer (50 mM Tris, 10 mM EDTA, pH 8.0). The cell resuspension was agitated at a temperature of 8-10° C. to fully re-suspend ($OD_{600}$=23 units) the cells and ensure homogeneity of the resultant cell slurry.

Heat treatment was carried out using a pilot scale High Temperature Short Time (HTST) processing system (Armfield FT74-20-MkIII Tubular Heat Exchanger UHT/HTST System, Armfield Ltd, Ringwood, UK). The system allows configurable pre-heating, heating/hold and cooling (residence) times by adjusting the number of heat exchanger tubes used. A wide range of residence times can be achieved by varying the product (cell slurry) flow rate and by re-configuring the number of pre-heat, heat/hold and cooling tubes used. The Armfield FT74-20-MkIII Tubular Heat Exchanger System was configured and cleaned prior to use following the manufacturers protocols. The tubular heat exchanger used in this example comprised multiple sections of dual concentric 316 stainless steel tubes (tube diameter 8.1 mm (product side), overall diameter 15.8 mm, each tube section length 0.4 m, 15 bar (maximum) working pressure) with static mixers (Armfield FT74-21). Product (cell slurry) flows through the centre whilst the heating or cooling water flows through the outer tube. The system was configured with 4 'pre-heat tubes' (each 0.4 m length) to rapidly bring the cell slurry to the desired inlet temperature. These tubes were followed by 2 'heating/hold tubes' (each 0.4 m length) which brought the cell slurry up to the required holding temperature. The desired hold temperature profile was controlled by automatic adjustment of the temperature of the pressurised heating water supplied to the pre-heat and hold tubes of the heat exchanger. The hold/residence time was varied by manually adjusting the cell slurry flow rate through the heat treatment apparatus. The cell slurry was then passed through 6 cooling tubes (each 0.4 m length) where the slurry was rapidly cooled prior to collection of the heat treated cell slurry product from each of the heat treatment processing conditions. Cooling water was provided to the cooling tubes of the heat exchanger. Temperature sensors/monitors were located at the product inlet to the heat treatment apparatus (T1), at the exit of the pre-heat/inlet of the heat/hold tubes (T2) and the exit of the heat/hold tubes (T3) and outlet from $4^{th}$ cooling tube (T4). The output from sensor T2 was used to control the flow and temperature of the hot water supplied to the pre-heat and hold tube heat exchangers. For each heat treatment 'condition' (described in Table 1) the system was flushed with at least two volumes of cell slurry before collecting heat treated material to represent the heat treatment conditions being examined. The temperature of the heat treated material collected from the system was between 15-20° C., i.e. close to the temperature of the cooling water used to supply the cooling tubes. It will be evident to those skilled in the art how reducing the temperature of the cooling water supplied to the heat exchanger would reduce the outlet temperature of the heat treated material yet further if required. A sample was taken from each of the heat treatment processing conditions, centrifuged to separate the supernatant from the cell debris and the supernatant containing the extracted pDNA stored frozen at −20° C. for later analysis. FIG. 1 provides a schematic of the layout of the heat treatment apparatus configured as used in this example. Cell slurry flow rates, residence times and heat treatment temperatures used are presented in Table 1. The residence times were estimated by considering total pipe volume (including bends) and displacement due to the static mixers using data provided by the manufacturer (Armfield).

TABLE 1

| | | Flow rates, residence times and heat treatment temperatures | | | | | |
|---|---|---|---|---|---|---|---|
| Condition | Flow Rate (L/h) | Hold Tube Residence Time Estimate (seconds) | T1 (° C.) Cell Slurry Inlet | T2 (° C.) Hold Tube(s) Inlet | T3 (° C.) Hold Tube(s) Outlet | Average Hold Temp ((T2 + T3)/2) (° C.) | T4 (° C.) (at outlet of $4^{th}$ cooling tube) |
| A | 11.7 | ~15 | 12 | 120 | 124 | 122 | 19 |
| B | 19.4 | ~9 | 14 | 120 | 123 | 121.5 | 18 |
| C | 29.2 | ~6 | 12 | 117 | 127 | 122 | 38 |
| D | 7.6 | ~23 | 15 | 120 | 125 | 122.5 | 14 |

The cell pellet sample (cells from fermentation harvest prior to heat treatment) and clarified supernatant samples (post heat treatment) were thawed and analysed for supercoiled pDNA. Plasmid DNA was extracted, to provide a positive control, from the fermenter harvest sample using a plasmid preparation kit (Qiagen catalogue number 12123) following the manufacturers protocol. The pDNA positive control sample and supernatant samples collected post heat treatment were then analysed using gel electrophoresis using a 1% agarose gel visualised using Ethidium bromide. The supernatant samples were run on the agarose gel both undiluted and diluted (⅕). The results are presented in FIG. 2.

The results demonstrate that DNA was recovered following heat treatment conditions A, B, C and D but the recovered DNA was not intact. The DNA runs as a smear of differently sized fragments (Lanes 3-6). The DNA fragment size range decreases with increased incubation time further indicating that the heat treatments 'Condition A, B, C and D' had damaged the pDNA. The pDNA extracted from the fermentation harvest cell pellet sample indicates that supercoiled pDNA was present in the cells prior to the heat treatments carried out in this example. The diluted supernatant sample confirmed that the smear observed in Lanes 3-6 was not a result of gel overloading.

EXAMPLE 1

Batch fermentation (15 L) using CLD 327 was repeated as described in the Comparative Example. Samples were taken throughout the fermentation for measurement of cell growth ($OD_{600}$). The fermentation was continued until the $OD_{600}$ reached ~30 units (prior to glycerol depletion). A sample of the fermenter culture was taken, centrifuged to separate the cell pellet from the supernatant and the cell pellet stored frozen at −20° C. The fermenter vessel contents were then cooled to ~10° C. and transferred to 1 L sealable centrifuge bottles and the cells collected by batch centrifugation at 8-12° C. The recovered cell pellets were re-suspended to a volume of 12 L using cold (2-8° C.) buffer (50 mM Tris, 10 mM EDTA, pH 8.0). The cell resuspension was agitated at a temperature of 8-10° C. to fully re-suspend ($OD_{500}$=27 units) the cells and ensure homogeneity of the resultant cell slurry.

Heat treatment was carried out using the pilot scale High Temperature Short Time (HTST) processing system described in the Comparative Example, except as noted below. The system was configured and cleaned prior to use following the manufacturers protocols. The system was configured with 4 'pre-heat tubes' to rapidly bring the cell slurry to the desired inlet temperature. These tubes were followed by a single 'heating/hold tube' which brought the cell slurry up to the required holding temperature. The desired hold temperature profile was controlled by automatic adjustment of the temperature of the pressurised heating water supplied to the pre-heat and hold tube heat exchangers. The hold/residence time was varied by manually adjusting the cell slurry flow rate through the heat treatment apparatus. The cell slurry was then passed through 6 cooling tubes where the slurry was rapidly cooled prior to collection of the heat treated cell slurry product from each of the heat treatment processing conditions. Cooling water was provided to the cooling tube heat exchangers. Temperature sensors/monitors were located at the product inlet to the heat treatment apparatus (T1), at the exit of the pre-heat/inlet of the heat/hold tube (T2) and the exit of the heat/hold tube (T3) and outlet from the 4$^{th}$ cooling tube (T4). The output from sensor T2 was used to control the flow and temperature of the hot water supplied to the pre-heat and hold tubes of the heat exchanger. Tube diameters and lengths were the same as described in the Comparative Example. For each heat treatment 'condition' (described in Table 2) the system was flushed with at least two volumes of cell slurry before collecting heat treated material to represent the heat treatment conditions being examined. The temperature of the heat treated material collected from the system was between 15-20° C., i.e. close to the temperature of the cooling water used to supply the cooling tubes. It will be evident to those skilled in the art how reducing the temperature of the cooling water supplied to the heat exchanger would reduce the outlet temperature of the heat treated material yet further if required. A sample was taken from each of the heat treatment processing conditions, centrifuged to separate the supernatant from the cell debris and the supernatant containing the extracted pDNA stored frozen at −20° C. for later analysis. FIG. 3 provides a schematic of the layout of the heat treatment apparatus configured as used in this example. Cell slurry flow rates, residence times and heat treatment temperatures used are presented in Table 2. The residence times were estimated by considering total pipe volume (including bends) and displacement due to the static mixers used using data provided by the manufacturer (Armfield).

TABLE 2

| | | Flow rates, residence times and heat treatment temperatures | | | | | |
|---|---|---|---|---|---|---|---|
| Condition | Flow Rate (L/h) | Hold Tube Residence Time Estimate (seconds) | T1 (° C.) Cell Slurry Inlet | T2 (° C.) Hold Tube(s) Inlet | T3 (° C.) Hold Tube(s) Outlet | Average Hold Temp ((T2 + T3)/2) (° C.) | T4 (° C.) (at outlet of 4$^{th}$ cooling tube) |
| E | 17.5 | ~5 | 12.5 | 105 | 113 | 109 | 32 |
| F | 35.0 | ~2.5 | 12 | 99 | 107 | 103 | 41 |
| G | 27.2 | ~3 | 12 | 104 | 113 | 108.5 | 39 |
| H | 17.5 | ~5 | 12 | 100 | 107 | 103.5 | 24 |
| I | 17.5 | ~5 | 12 | 97 | 104 | 100.5 | 25 |
| J | 35.0 | ~2.5 | 12 | 92 | 101 | 96.5 | 38 |

The cell pellet sample (cells from fermentation harvest prior to heat treatment) and clarified supernatant samples (post heat treatment) were thawed and analysed for supercoiled pDNA. Plasmid DNA was extracted, to provide a positive control, from the fermenter harvest sample using a plasmid preparation kit (Machery-Nagel Nucleospin plasmid purification kit, catalogue number 740588250) following the manufacturers protocol. The pDNA positive control sample and supernatant samples collected post heat treatment were then analysed using gel electrophoresis using a 1% agarose gel visualised using Ethidium bromide. The results are presented in FIG. 4.

The data presented in FIG. 4 demonstrates that the heat treatment conditions described in Example 1 successfully released DNA including supercoiled plasmid DNA from the cell slurry.

EXAMPLE 2

The procedure of Example 1 was repeated, but employing the conditions set out in Table 3 below.

TABLE 3

| Condition | Flow Rate (L/h) | Hold Tube Residence Time Estimate (seconds) | T1 (° C.) Cell Slurry Inlet | T2 (° C.) Hold Tube(s) Inlet | T3 (° C.) Hold Tube(s) Outlet | Average Hold Temp ((T2 + T3)/2) (° C.) | T4 (° C.) (at outlet of 4$^{th}$ cooling tube) |
|---|---|---|---|---|---|---|---|
| K | 11.0 | 8.8 | 23 | 119 | 121 | 120 | 21 |
| L | 11.0 | 8.8 | 23 | 114 | 116 | 115 | 21 |
| M | 18.2 | 5.4 | 23 | 114 | 116 | 115 | 30 |
| N | 22.7 | 4.3 | 23 | 114 | 118 | 116 | 37 |
| O | 30.3 | 3.2 | 23 | 103 | 108 | 105.5 | 44.5 |
| P | 23 | 4.2 | 23 | 104 | 109 | 106.5 | 39 |
| Q | 31.7 | 3.1 | 14 | 117 | 120 | 108.5 | 52 |

A sample of supernatant collected post heat treatment from Conditions L to X, together with a sample of supernatant from Example 1, Condition E was transformed into competent *E. coli* cells. Serial dilutions of the transformed cells onto kanamycin selective agar plates. Given that the plasmid contains a kanamycin resistance marker, the detection of viable cells indicates that the supernatant contained intact plasmid. The results of this assay showed that each of the samples tested contained intact plasmid DNA.

The invention claimed is:

1. A process for the extraction of pDNA from a cell, which comprises heating a liquid comprising the cell to an average temperature of from 95° C. to about 120° C. for a time of less than 10 seconds.

2. A process according to claim 1, wherein the liquid is heated in a flow-through apparatus.

3. A process for the extraction of pDNA from a cell, which comprises heating a liquid comprising the cell in a flow-through apparatus to an temperature of 95° C. or more, provided that the liquid is not heated to an average temperature of greater than 120° C. for longer than 5 seconds.

4. A process according to claim 3, wherein the liquid comprising the cell to an average temperature of from 95° C. to about 120° C. for a time of less than 10 seconds.

5. A process according to claim 4, wherein the liquid is maintained at a temperature of greater than 95° C. for up to 6 seconds.

6. A process according to claim 3, wherein the process employs flow-through apparatus comprising a heating zone, where the liquid is heated from the initial temperature to a temperature of greater than 95° C., a holding zone, where the liquid is held at a temperature of greater than 95° C., and a cooling zone, where the liquid is cooled.

7. A process according to claim 6, wherein the initial temperature of the liquid is from 2° C. to 45° C.

8. A process according to claim 6, wherein the liquid is cooled to a temperature of from 10° C. to 45° C.

9. A process according to claim 1, wherein the liquid is maintained at a temperature of above 95° C. and up to 110° C. for from 2 to 6 seconds.

10. A process according to claim 1 or 3, wherein the liquid is maintained at a temperature of from 115° C. to 120° C. for from 1 to 3 seconds.

11. A process according to claim 1 or 3, wherein the liquid is maintained at a temperature of from 120° C. to 130° C. for from 0.5 to 1.5 seconds.

12. A process according to claim 1 or 3, wherein the pDNA is extracted in the supercoiled isoform.

13. A process according to claim 1 or 3, wherein the pDNA is extracted in the open circular isoform.

14. A process according to claim 13, wherein the open circular isoform pDNA is subsequently converted to the supercoiled isoform.

15. A process according to claim 2, wherein the process employs flow-through apparatus comprising a heating zone, where the liquid is heated from the initial temperature to a temperature of greater than 95° C., a holding zone, where the liquid is held at a temperature of greater than 95° C., and a cooling zone, where the liquid is cooled.

16. A process according to claim 15, wherein the initial temperature of the liquid is from 2° C. to 45° C.

17. A process according to either claim 15 or 16, wherein the liquid is cooled to a temperature of from 10° C. to 45° C.

18. A process according to claim 1, wherein the liquid is maintained at a temperature of greater than 95° C. for up to 6 seconds.

* * * * *